US010548915B2

(12) United States Patent
Tsay et al.

(10) Patent No.: US 10,548,915 B2
(45) Date of Patent: Feb. 4, 2020

(54) COMBINATION THERAPY FOR EV71 INFECTION

(71) Applicant: SUN JET BIOTECHNOLOGY INC., Taipei (TW)

(72) Inventors: Yeou Guang Tsay, Taipei (TW); Szu-Hao Kung, Taipei (TW)

(73) Assignee: SUN JET BIOTECHNOLOGY INC., Taipei (TW)

( * ) Notice: Subject to any disclaimer, the term of this patent is extended or adjusted under 35 U.S.C. 154(b) by 0 days.

(21) Appl. No.: 15/762,949

(22) PCT Filed: Sep. 26, 2016

(86) PCT No.: PCT/CN2016/100186
§ 371 (c)(1),
(2) Date: Mar. 23, 2018

(87) PCT Pub. No.: WO2017/050297
PCT Pub. Date: Mar. 30, 2017

(65) Prior Publication Data
US 2018/0264028 A1 Sep. 20, 2018

Related U.S. Application Data

(60) Provisional application No. 62/232,779, filed on Sep. 25, 2015.

(51) Int. Cl.
*A61K 31/7135* (2006.01)
*A61K 31/138* (2006.01)
*A61K 31/7048* (2006.01)
*A61K 31/167* (2006.01)
*A61K 31/4745* (2006.01)

(52) U.S. Cl.
CPC ........ *A61K 31/7135* (2013.01); *A61K 31/138* (2013.01); *A61K 31/167* (2013.01); *A61K 31/4745* (2013.01); *A61K 31/7048* (2013.01)

(58) Field of Classification Search
CPC . A61K 31/138; A61K 31/167; A61K 31/7135
See application file for complete search history.

(56) References Cited

U.S. PATENT DOCUMENTS 7,544,712 B1 *  6/2009  Hsu ................. A61K 31/33
                                                    424/204.1

FOREIGN PATENT DOCUMENTS

| CN | 101869574 A | 10/2010 |
| CN | 102595894 A | 7/2012 |
| CN | 103479662 A | 1/2014 |
| CN | 103784451 A | 5/2014 |

OTHER PUBLICATIONS

Andrews (International Journal of Parasitology: Drugs and Drug Resistance; 4, 2014, 95-111).*
Bentfeld (British Journal of Pharmacology; Sep. 1977, 61 (1); 19-27; Abstract).*
International Search Report for PCT/CN2016/100186 dated Dec. 28, 2016.
Written Opinion of the International Searching Authority for PCT/CN2016/100186 dated Dec. 28, 2016.

* cited by examiner

*Primary Examiner* — Pancham Bakshi
(74) *Attorney, Agent, or Firm* — Birch, Stewart, Kolasch & Birch, LLP

(57) ABSTRACT

The present invention is related to a combination for treating an EV71 infection, which comprises two or more compounds at each's non-effective level and provides an unexpected synergistic activity against EV71 replication, wherein the compound is selected from the group consisting of auranofin, ouabain, emetine, niclosamide, and S-(+)-fluoxetine.

10 Claims, 6 Drawing Sheets
Specification includes a Sequence Listing.

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
tgtagatcag gccgatgagt ca                22

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
catgtccaca ttagagcgtc ctat               24

COMBINATION THERAPY FOR EV71 INFECTION

CROSS REFERENCE TO RELATED APPLICATIONS

This application is the National Phase of PCT International Application No. PCT/CN2016/100186, filed on Sep. 26, 2016, which claims priority under 35 U.S.C. 119(e) to U.S. Provisional Application No. 62/232,779, filed on Sep. 25, 2015, all of which are hereby expressly incorporated by reference into the present application.

FIELD OF THE INVENTION

The present invention is related to a combination therapy for EV71 infection.

BACKGROUND OF THE INVENTION

Enterovirus type 71 (EV71) has caused several major outbreaks. It usually infects young children and causes hand, foot and mouth disease. It also has the potential to cause severe neurological diseases. Until now, there is no antiviral agent known to be effective in treating EV71 infection.

EV71 was first isolated in California, USA in 1969 (Wang, J. R. et al., Change of Major Genotype of Enterovirus 71 in Outbreaks of Hand-Foot-and-Mouth Disease in Taiwan between 1998 and 2000. Journal of Clinical Microbiology 40, 10-15, 2002). It has become an important clinical issue around Asia-Pacific region (McMinn et al., Phylogenetic Analysis of Enterovirus 71 Strains Isolated during Linked Epidemics in Malaysia, Singapore, and Western Australia. Journal of Virology 75, 7732-7738, 2001). EV71 usually infects young children with age of 3 years or younger. It may cause rashes, severe neurological disease and hand, foot and mouth disease (HFMD) (Repass et al., Hand, foot, and mouth disease: identifying and managing an acute viral syndrome. Cleveland Clinic journal of medicine 81, 537-543, 2014). In Taiwan, many big outbreaks with fatal cases have been reported since 1998. Hence, it is important to develop vaccines for prevention and effective drugs for treatment.

Various EV71 vaccine candidates are being researched in animal models, including live-attenuated virus vaccine, recombinant VP1 vaccine, synthetic peptide vaccine and virus-like particle vaccine (Kung et al., Update on the development of enterovirus 71 vaccines. Expert Opinion on Biological Therapy 14, 1455-1464, 2014). Recently, a phase III clinical trial of an EV71 vaccine has been completed in China, and two phase I clinical trials have been completed in Taiwan and Singapore respectively. They are all inactivated whole-virus alum-adjuvant vaccines which separately use isolated C4 genotype virus as vaccine strain (Liang and Wang, EV71 vaccine, an invaluable gift for children. Clin Trans Immunol 3, e28, 2014). Their protective efficacies were over 90% on EV71-associated HFMD and over 80% on other EV71-associated diseases.

Accordingly, it is desirable to develop a novel therapeutics for EV17 infections.

SUMMARY OF THE INVENTION

It is unexpectedly discovered in the present invention a combination of five drugs at their respective non-effective level provides strong synergism against EV71 replication, particularly appeared to have universal anti-EV71 effects in various cells susceptible to EV71 infection. We believed that our de novo deduction of cocktail therapies can not only provide an effective anti-EV71 recipes, but also can be a powerful tool in treating various viral infection.

Accordingly, one aspect of the invention provides a combination for treating an EV71 infection, which comprises two or more compounds at each's non-effective level to provide a synergistic activity against EV71 replication, wherein the compound is selected from the group consisting of auranofin, ouabain, emetine, niclosamide, and S-(+)-fluoxetine.

Another aspect of the invention pertains to a method for treating an EV71 infection, comprising administering to a subject in need thereof a therapeutically effective amount of the combination according to the invention.

A further aspect of the invention pertains to a method for treating hand, foot and mouth disease (HFMD), comprising administering to a subject in need thereof a therapeutically effective amount of the combination according to the invention.

A yet aspect of the invention pertains to a pharmaceutical composition for treating an EV71 infection, comprising a therapeutically effective amount of the combination according to the invention.

A further yet aspect of the invention pertains to a pharmaceutical composition for treating hand, foot and mouth disease (HFMD), comprising a therapeutically effective amount of the combination according to the invention.

These and other objects, along with advantages and features of embodiments of the present invention herein disclosed, will become more apparent through references to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

The foregoing summary, as well as the following detailed description of the invention, will be better understood when read in conjunction with the appended drawing. In the drawings.

DESCRIPTION OF THE INVENTION

Figure 1:
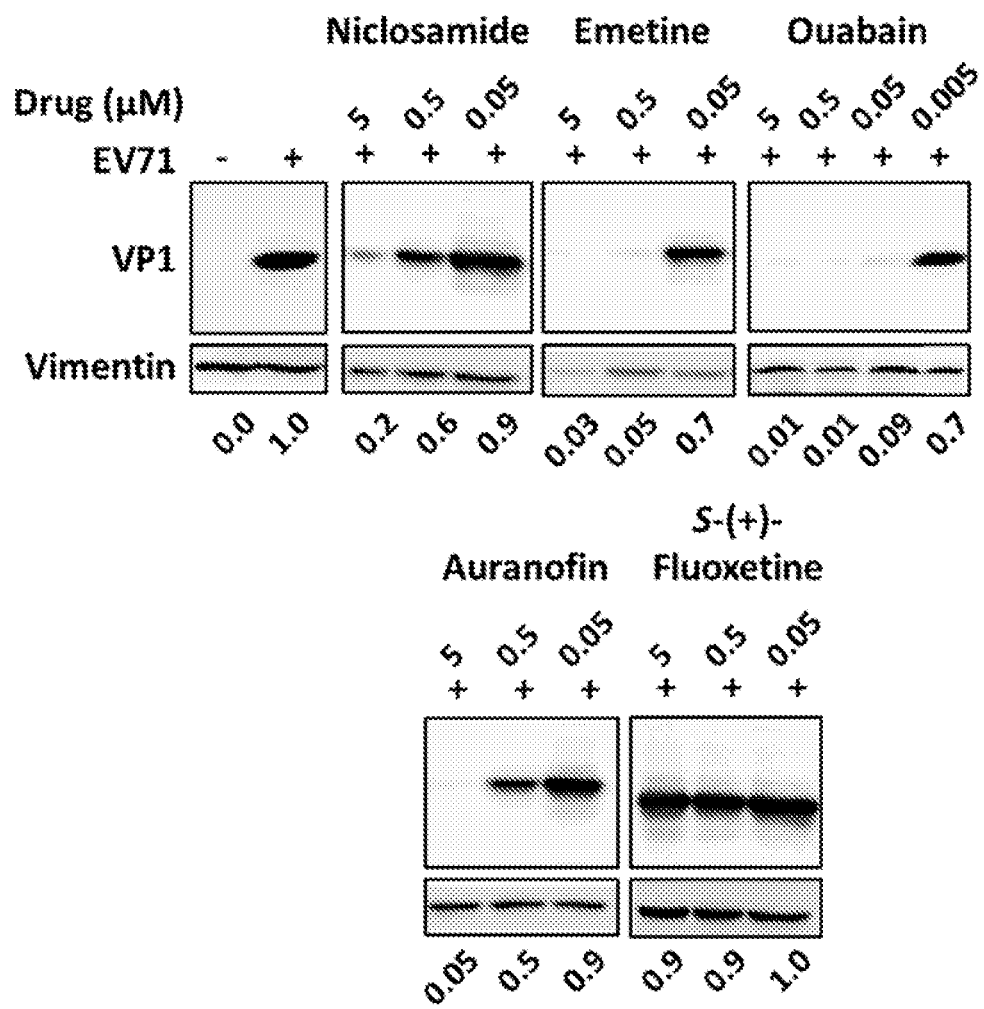
FIG. 1 provides the results of determination of the anti-EV71 effects of the combination according to the invention under different concentrations, wherein RD cells were infected with EV71 at a multiplicity of infection (MOI) of 5 in the presence of indicated compound at 5, 0.5 or 0.05 µM; for ouabain, a fourth concentration 0.005 µM was used; the numbers beneath gel lanes indicate the ratios between VP1 and vimentin signals with western blot; and these ratios are normalized according to that for non-treated, EV71-infected cells.
Figure 2:
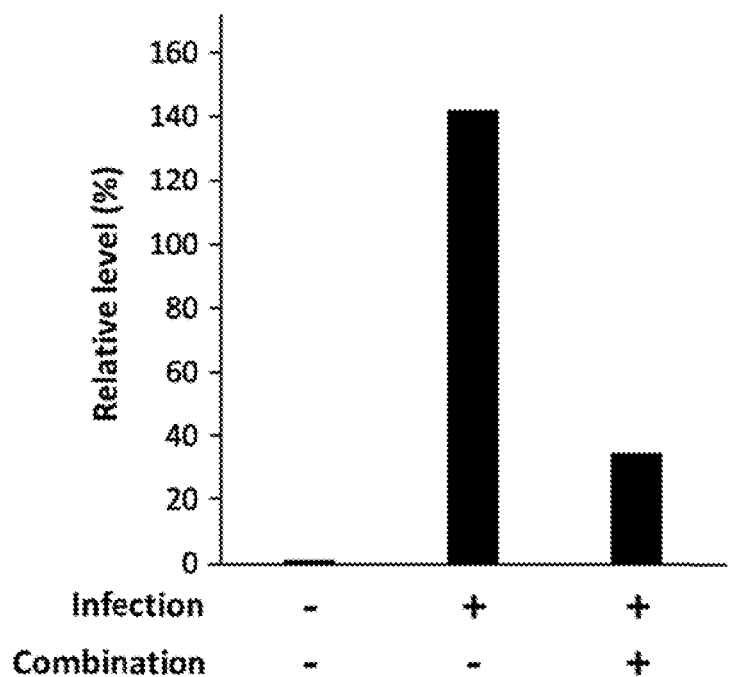
FIG. 2 provides the results of the quantification analyses of EV71 RNA in cells with or without five-compound treatment; wherein RD cells were infected by EV71 at a multiplicity of infection (MOI) of 5 with or without five-compound combination. After 4-hour incubation, the cellular RNAs were isolated. The forward and reverse primers were designed for amplification of 5'-UTR of EV71, and the internal control was GAPDH. Real-time reverse-transcription polymerase chain reaction (qRT-PCR) was applied to detect EV71 RNA expression. The relative levels of EV71 RNA was measured by ΔCt method. Niclosamide, emetine, auranofin and S-(+)-fluoxetine were used at 0.05 µM; ouabain was used at 5 nM.
Figure 3:
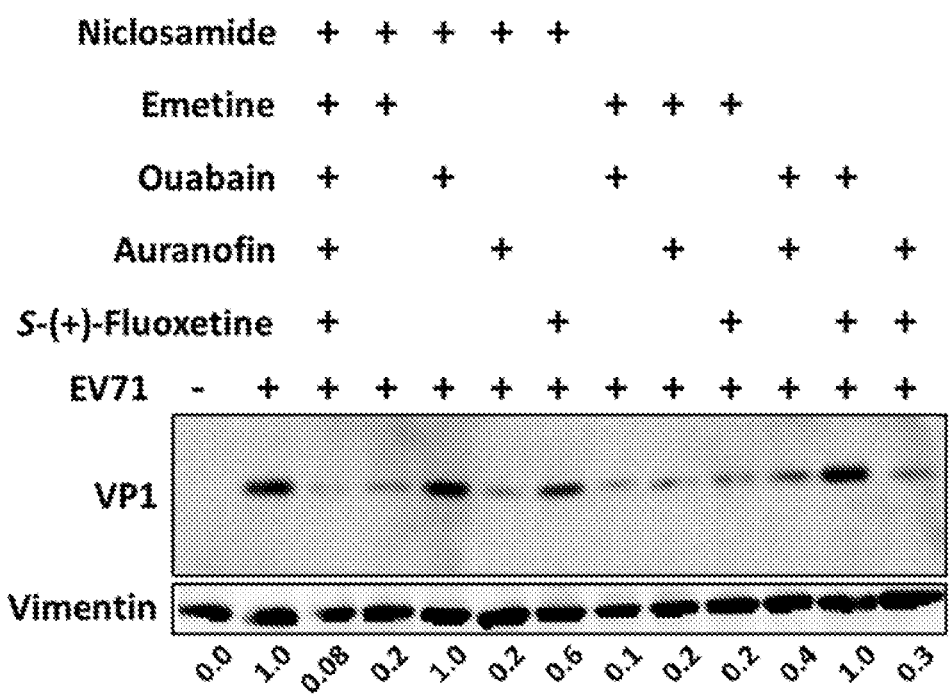
FIG. 3 provides the western blot analyses with VP1 antibodies of EV71-infected RD cells in the presence of various binary combinations according to the invention; wherein RD cells were infected with EV71 in the presence of the combination containing two of five compounds; and the numbers at the bottom of the blot indicate the relative VP1 expression over non-treated control. Niclosamide, emetine, auranofin and S-(+)-fluoxetine were used at 0.05 µM; ouabain was used at 5 nM.
Figure 4:
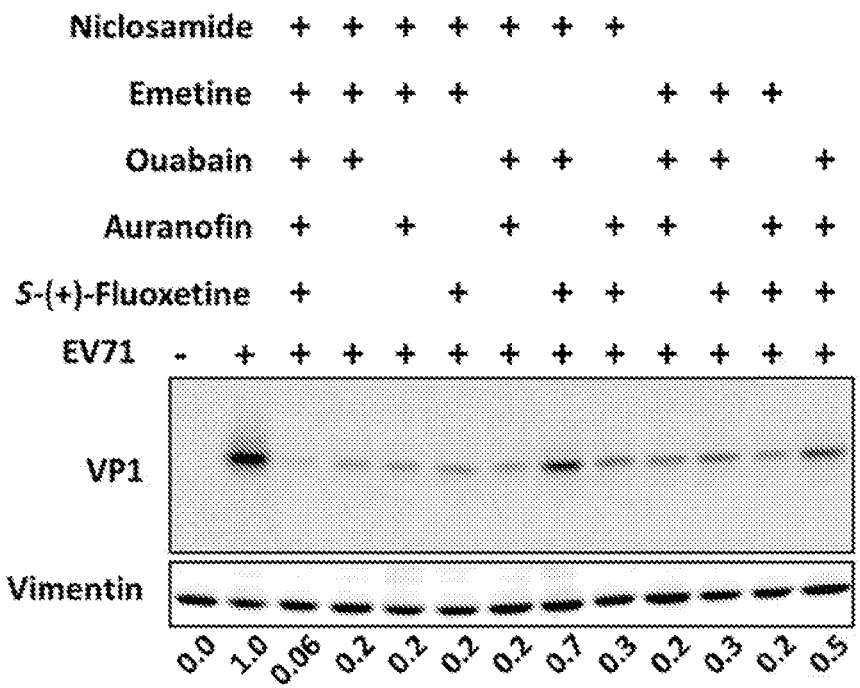
FIG. 4 provides the anti-VP1 western blot analyses of proteins from EV71-infected RD cells in the presence of various ternary combinations according to the invention. RD cells were infected with EV71 in the presence of the combination containing three of five compounds. The numbers at the bottom of the blot indicate the relative VP1 expression over non-treated control. Niclosamide, emetine, auranofin and S-(+)-fluoxetine were used at 0.05 µM; ouabain was used at 5 nM.
Figure 5:
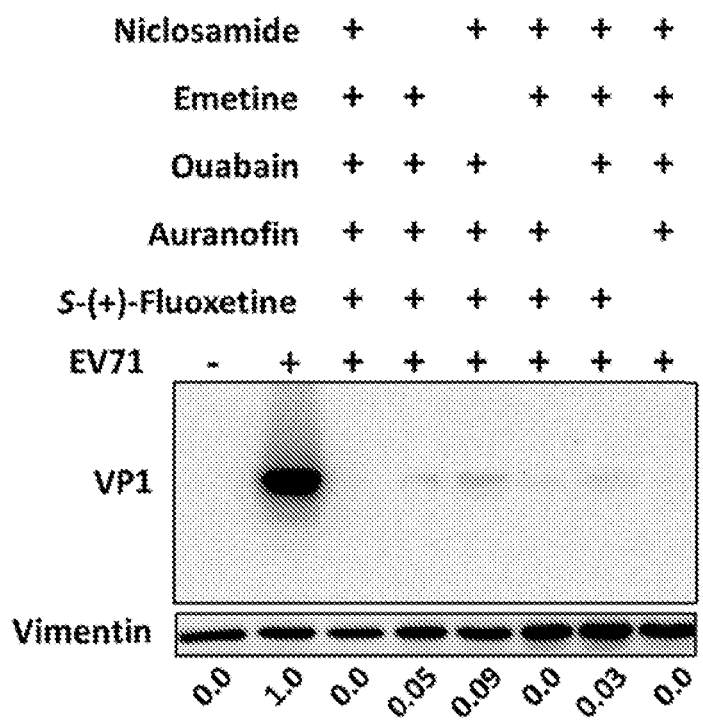
FIG. 5 provides the anti-VP1 western blot analyses of proteins from EV71-infected RD cells in the presence of quaternary combinations according to the invention. RD cells were infected with EV71 in the presence of the combination containing four of five compounds. The numbers at the bottom of the blot indicate the relative VP1 expression over non-treated control. Niclosamide, emetine, auranofin and S-(+)-fluoxetine were used at 0.05 µM; ouabain was used at 5 nM.
Figure 6:
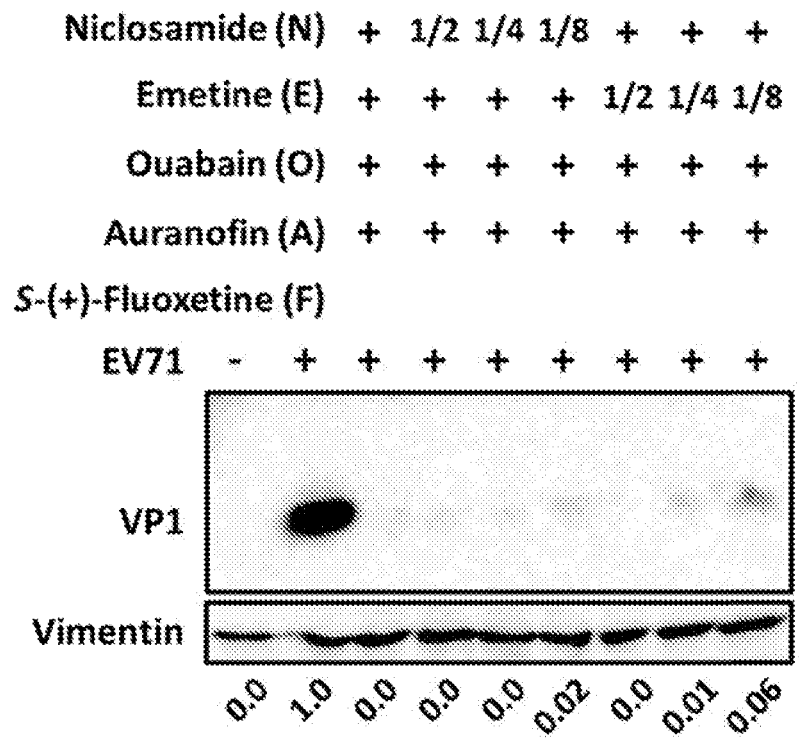
FIG. 6 provides the anti-VP1 western blot analyses of proteins from EV71-infected RD cells in the presence of indicated N-E-O-A combinations made by serial dilutions of niclosamide or emetine. The numbers at the bottom of the blot specify the VP1 expression relative to the non-treated control. The auranofin and ouabain were used at 0.05 µM and 5 nM, respectively. The fractions are the dilution ratio of the chemical drugs. For niclosamide and emetine, ½, ¼ and ⅛ mark the concentrations of 25, 12.5 and 6.25 nM respectively.
Figure 7:
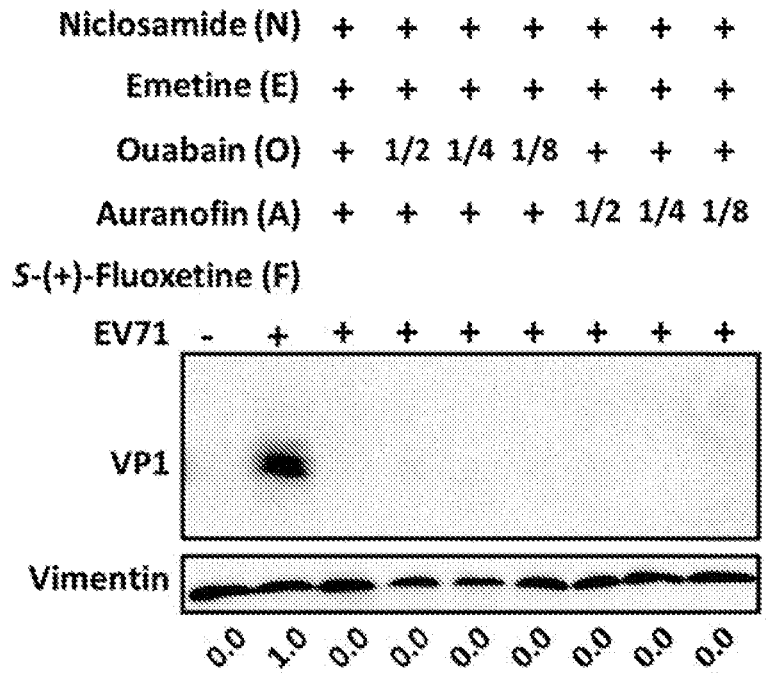
FIG. 7 provides the anti-VP1 western blot analyses of proteins from EV71-infected RD cells in the presence of indicated N-E-O-A combinations made by serial dilutions of ouabain or auranofin. The numbers at the bottom of the blot specify the VP1 expression relative to the non-treated control. The niclosamide and emetine concentrations were 0.05 µM. For ouabain, ½, ¼ and ⅛ was 2.5, 1.25 and 0.6 nM respectively. For auranofin, the same set of fractions denote 25, 12.5 and 6.25 nM respectively.
Figure 8:
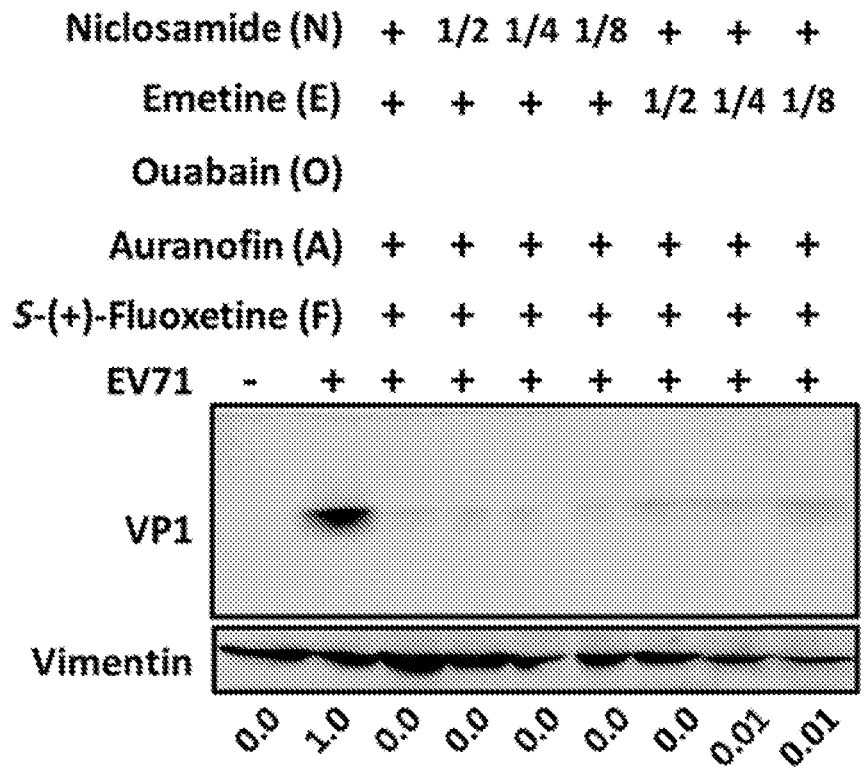
FIG. 8 provides the anti-VP1 western blot analyses of proteins from EV71-infected RD cells in the presence of indicated N-E-A-F combinations made by serial dilutions of niclosamide or emetine. The numbers at the bottom of the blot specify the VP1 expression relative to the non-treated control. The auranofin and fluoxetine concentrations were 0.05 µM. For niclosamide and emetine, ½, ¼ and ⅛ mean 25, 12.5 and 6.25 nM respectively.
Figure 9:
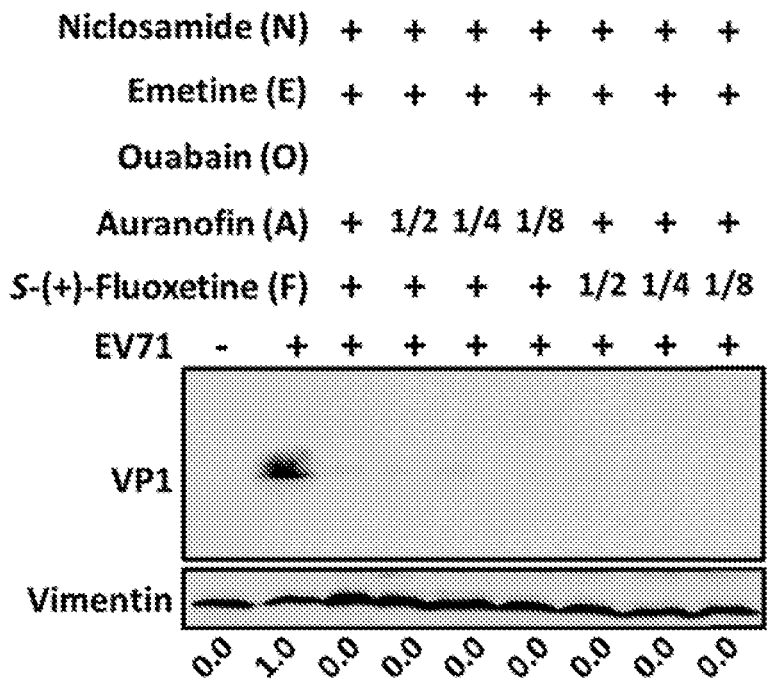
FIG. 9 provides the anti-VP1 western blot analyses of proteins from EV71-infected RD cells in the presence of indicated N-E-A-F combinations made by serial dilutions of auranofin or fluoxetine. The numbers at the bottom of the blot specify the VP1 expression relative to the non-treated control. The niclosamide and emetine concentrations were 0.05 µM. For auranofin and fluoxetine, ½, ¼ and ⅛ denote 25, 12.5 and 6.25 nM respectively.
Figure 10:
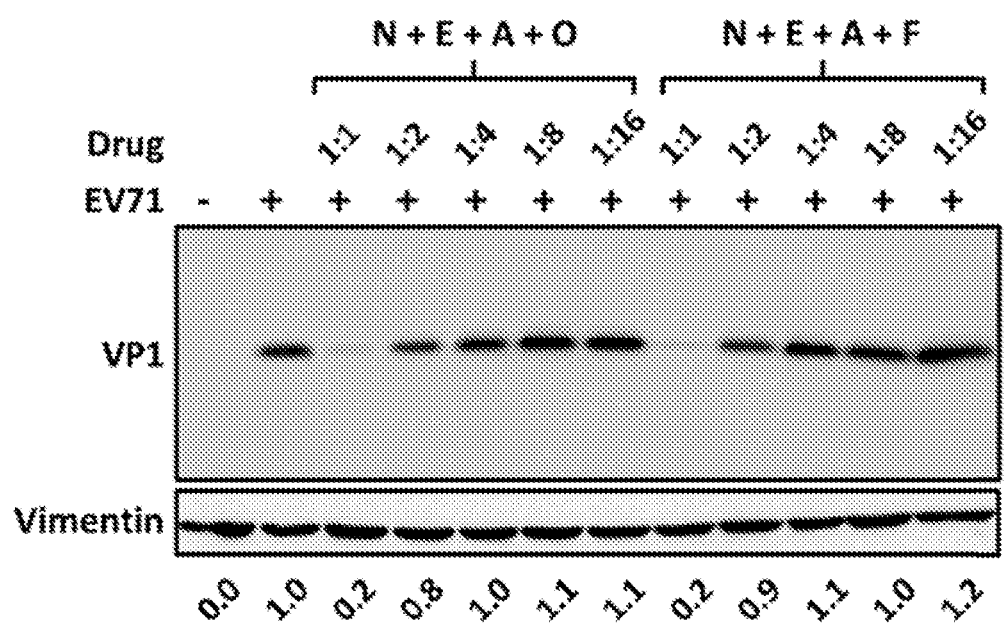
FIG. 10 shows the anti-VP1 western blot analyses of proteins from EV71-infected RD cells in the presence of serially diluted N-E-A-O or N-E-A-F combinations. The numbers at the bottom of the blot specify the VP1 expression relative to the non-treated control. For 1:1 condition, the N, E, A and F concentrations are 0.05 µM and O concentration is 5 nM. N: niclosamide; E: emetine; A: auranofin; O: ouabain; F: fluoxetine.

Unless defined otherwise, all technical and scientific terms used herein have the same meaning as commonly understood by a person skilled in the art to which this invention belongs.

A list of abbreviations as used herein is provided in Table 1 below

TABLE 1

LIST OF ABBREVIATIONS

| Abbreviation | Full Name |
|---|---|
| A | auranofin |
| E | emetine |
| ESBL | extended-spectrum β-lactamase |
| EV71 | enterovirus type 71 |
| F | S-(+)-fluoxetine |
| HCV | hepatitis C virus |
| HFMD | hand, foot and mouth disease |
| HIV | human immunodeficiency virus |
| HTS | high-throughput screening |
| IRES | internal ribosome entry site |
| MOI | multiplicity of infection |
| mRNA | messenger RNA |
| MRSA | methicillin-resistant *Staphylococcus aureus* |
| N | niclosamide |
| NNRTI | non-nucleoside reverse transcriptase inhibitors |
| NRTI | nucleoside reverse transcriptase inhibitor |
| O | ouabain |
| PCBP/PABP | poly(C)/poly(A)-binding protein |
| qRT-PCR | real-time reverse transcription polymerase chain reaction |
| R&D | research and development |
| RD | rhabdomyosarcoma |
| SAR | structure-activity relationship |
| UTR | untranslated region |

To date, researches often chose a single viral protein as a drug target, including structural and non-structural proteins. While there are a number of compounds have been shown to inhibit EV71 replication, none of them has been validated by human clinical trials. Because the EV71 RNA genome is synthesized by its RNA-dependent RNA polymerase, which does not have proofreading activity, mutations in the newly synthesized viral genome are frequently generated during replication. Thus, EV71 variants that present antiviral resistance phenotypes could often be selected during antiviral treatment. As a result, the development of specific antiviral strategies against EV71 need to be revised. The present invention provides an alternative approach that attempts to develop anti-EV71 cocktail therapy through synergism by multiple partial inhibitions.

The present invention provides a combination for treating an EV71 infection, which comprises two or more compounds at each's non-effective level and provides an unexpected synergistic activity against EV71 replication, wherein the compound is selected from the group consisting of auranofin, ouabain, emetine, niclosamide, and S-(+)-fluoxetine.

In one embodiment of the invention, some examples of the combination providing a synergistic activity against EV71 replication include:
niclosamide and emetine;
niclosamide and auranofin;
niclosamide and ouabain;
niclosamide and S-(+)-fluoxetine;

emetine and ouabain;
emetine and auranofin;
emetine and S-(+)-fluoxetine;
ouabain and auranofin;
ouabain and S-(+)-fluoxetine; and
auranofin and S-(+)-fluoxetine;

In addition, the invention provides a method or pharmaceutical composition for treating an EV71 infection.

The invention also provides a method or pharmaceutical composition for treating hand, foot and mouth disease (HFMD).

The term "therapeutically effective amount" as used herein refers to a sufficient amount of each of the compounds to provide the desired therapeutic effects, or the induction of a particular type of response. The theraoeytucally effective amount required varies from subject to subject, depending on the disease state, physical conditions, age, sex, species and weight of the subject, etc. However, an appropriate effective amount can be determined by one of ordinary skill in the art using only routine experimentation.

As used herein, the term "non-effective level per day" refers to a level or dosage of a compound per day for a human subject, which cannot provide the desired therapeutic effects, or the induction of a particular type of response for a human subject having an average body weight of 60 kg. In one embodiment, the non-effective level for each compound is below a therapeutically effective amount per day for a human subject.

In one example of the invention, the non-effective level of niclosamide is below 2 mg per day for a human subject.

In one example of the invention, the non-effective level of ouabain is below 0.3 mg per day for a human subject.

In one example of the invention, the non-effective level of auranofin is below 6 mg per day for a human subject.

In one example of the invention, the non-effective level of emetine is below 60 mg per day for a human subject.

In one example of the invention, the non-effective level of S-(+)-fluoxetine is below 20 mg per day for a human subject.

The pharmaceutical composition of the present invention can be manufactured by conventionally known methods with one or more pharmaceutically acceptable carriers. The term "pharmaceutically acceptable carrier" as used herein encompasses any of the standard pharmaceutical carriers. The pharmaceutical composition of the present invention may be constituted into any form suitable for the mode of administration selected. For example, compositions suitable for oral administration include solid forms, such as pills, capsules, granules, tablets, and powders, and liquid forms, such as solutions, syrups, elixirs, and suspensions. Forms useful for topical administration include cream, ointment, gel, suspension, drops, emulsions, skin patches.

In addition to standard carriers, an oral pharmaceutical composition of the present invention may be supplemented with one or more excipients that are normally employed in oral formulations, such as surfactants, inhalants, solubilizers, stabilizers, emulsifiers, thickeners, coloring agents, sweetening agents, flavoring agents, and preservatives. Such excipients are well known to those skilled in the art.

EXAMPLES

Materials and Methods

Antibodies—Used antibodies included rabbit anti-VP1 (GTX70007, 1:2000, GeneTex), mouse anti-vimentin (sc-6260, 1:1000, Santa Cruz).

Drugs—Chemical drugs used were auranofin (Cat. #A6733, Sigma), emetine (Cat. #E2375, Sigma), niclos- amide (Cat. #N3510, Sigma), ouabain (Cat. #O3125, Sigma), S-(+)-fluoxetine (Cat. #F1553, Sigma).

Cell lines, viruses and viral infection—RD (Human rhabdomyosarcoma, ATCC® CCL-136™) cells were grown in Dulbecco's modified Eagle's medium (Sigma, USA) containing 10% fetal bovine serum (Invitrogen, USA), at 5% $CO_2$ and 37° C. EV71 strain 4643/TW/1998 (GeneBank accession number 1N544418.1) was kindly provided by Dr. Lih-Hwa Hwang at National Yang-Ming University, Taiwan. Viruses were added to RD cells which were cultured in DMEM containing 2% FBS. The newly generated viruses were titrated by cytopathology assay. For viral infection, cells were seeded at 80% confluency in 6-well dishes and grown overnight. Before challenge with viruses of 5 multiplicity of infection (MOI), old medium was replaced with serum-free medium. After 1 h adsorption of viruses, infected cells were cultured in DMEM with 10% FBS.

Real-time reverse-transcription polymerase chain reaction—The real-time reverse transcription polymerase chain reaction (qRT-PCR) was carried out using the StepOnePlus™ Real-Time PCR System (applied Biosystems, USA) with Fast SYBR® Green Master Mix (Applied Biosystems, USA) and ReverAid First Strand cDNA Synthesis Kit (Thermo Scientific, USA). RT assay was performed according to the manufacturer's instructions. EV71-specific forward primer (5'-TGTAGATCAGGCCGATGAGTCA-3') and reverse primer (5'-CATGTCCACATTAGAGCGTC-CTAT-3') primers targeting a conserved 5'-UTR region. We used GAPDH, a housekeeping gene, for internal control. qPCR assay was carried out in a 10 μL volume consisting of 5 μL of 2× Fast SYBR® Green Master Mix, 0.2 μL of 10 μM/μL of each oligonucleotide primer and 4.6 μL of 2.5 ng/μL RNA extracted from samples. Comparative ΔCt method with melt curve and fast mode were selected as the RUN setting of StepOnePlus™Real-Time PCR System for the target fragment amplification. The thermal cycling conditions were specified as follow: initial activation of AmpliTaq® Fast DNA Polymerase at 95° C. for 10 min; 40 cycles in two steps, 95° C. for 15 sec and 60° C. for 60 sec. At the end of the amplification cycles, melting temperature analysis was attained by a gradual increase in temperature (0.5° C./s) up to 95° C.

Western blotting—Protein extracted from RD cells were resolved with electrophoresis. Protein were blotted onto a nitrocellulose membrane eletrophoretically and incubated with indicated antibodies. The immunoreactive bands were visualized with LAS-4000 (FUJIFLIM).

Example 1 Selection of On-the-Market Drugs

Five on-the-market drugs, including niclosamide, emetine, ouabain, auronofin and S-(+)-fluoxetine, were chosen for further characterization of their pharmacological properties. In order to examine the dose response of the five on-the-market compounds in EV71 antagonism, How EV71 replication was affected under various concentrations of these agents were examined.

When each of these five compounds, except fluoxetine, was added at a concentration of 5 μM, the efficiency of EV71 replication based on VP1 expression was greatly compromised (FIG. 1). While the fluoxetine discrepancy probably means the difference between biological assays, our data largely validate the effectiveness of Kung's method in picking up anti-EV71 chemicals. Meanwhile, these data altogether also strongly suggest that our current assay has the capacity to test the inhibitory actions on EV71 replication by compounds as well as their combinations. For niclosamide and auranofin, prominent EV71 suppression was observed when each was applied at 5 μM as VP1 expression was only 0.2 and 0.05, respectively, of the non-treated infected cells (FIG. 1). When their levels decreased to 0.5 μM, the anti-EV71 effect was lessened accordingly with VP1 expression returning to 0.9~0.6. More importantly, when 0.005 μM was used, no detectable inhibition was seen with VP1 expression of 0.9. Thus, niclosamide and auranofin have strong anti-EV71 at 5 μM but minimal effects at 0.05 μM, showing adequate dose-response in EV71 suppression. Meanwhile, emetine and ouabain have stronger effects on VP1 expression. When 0.5-5 μM at emetine or 0.05-5 μM of ouabain was used individually, strong blockage of EV71 expression was observed. To see VP1 expression returning, emetine and ouabain needed to decrease to 0.05 and 0.005 μM, respectively (FIG. 1). In contrast, when only fluoxetine was used, there was no marked effect as 0.9-1.0 of VP1 expression was documented for all tested concentrations.

Example 2 Test for Synergistic Suppression on EV71 Replication

To test whether the above five compounds might have synergistic suppression on EV71 replication, the combinations containing all components at their non-inhibitory levels were used and their amounts were gradually increased until prominent effects were seen.

0.05 μM of niclosamide, emetine, auranofin and fluoxetine as well as 5 nM of ouabain were included in the combination. Intriguingly, we found that, even at their individual non-inhibitory doses, these five compounds have strong suppression of EV71 replication. Under this condition, only 30% of EV71 RNA (FIG. 2) and 8% of VP1 protein expressed (FIG. 3). Altogether, these data suggest that the synergism between these five compounds causes an unexpectedly high suppression of EV71 replication. Since synergism by these components in the five-compound list was the likely pharmacodynamic mechanism, the comprehensive analyses were performed to check how each component could interact with one another in the list. A thorough examination of all binary combinations on their anti-EV71 effects was conducted. While most of the combinations indeed decreased VP1 expression by 80 to 90%, some exerted mild suppression with a VP1 expression of 0.4-0.6. More importantly, with VP1 expression at 1.0, niclosamide (N)-ouabain (O) and ouabain (O)-fluoxetine (F) combinations showed little effects on EV71 replication (FIG. 3). Altogether, these data suggest that each component in the list indeed has specific interaction with one another in anti-EV71 efficacy. For example, while lacking synergism with niclosamide or fluoxetine, ouabain has moderate effects with auranofin and strong interaction with emetine. Also, these specific interactions suggest that the potency of a combination can be adjusted through specific inclusion of the compounds.

Example 3 Test for all Ternary and Quaternary Combinations According to the Invention To find the best combinations, a complete testing of all ternary and quaternary combinations were conducted.

While most of the ternary combinations could reduce VP1 expression by at least 70~80%, there were two recipes only showing moderate reduction (FIG. 6). The results by niclosamide (N)-ouabain (O)-fluoxetine (F) combination were particularly interesting. Since N-O and O-F combinations have no synergism (FIG. 5), we expected that the effect by N-O-F combination must result from N-F synergism. Indeed, N-O-F and N-F combinations has similar anti-EV71 activities (FIG. 3 and FIG. 4). Finally, we examined how quaternary combinations affected VP1 expression in EV71 replication. As expected, all of the quaternary combinations showed strong anti-EV71 effects, with N-E-A-F and N-E-O-A exhibiting a potency similar to the original five-compound recipe (FIG. 5). Interestingly, all the components are involved in constitution of maximal synergism; in other word, none of them can be omitted when strongest potency is aimed. Particularly, although fluoxetine at the correct dose range has little effects in this EV71 replication assay, its specific synergism with other compounds cannot be ignored in this assay.

Example 4 Test for the Non-Inhibitory Levels of Each Compound Used in the Combinations According to the Invention Inasmuch as all of the compounds have been tested at their non-inhibitory levels, these compounds used in these analyses have been relatively low, ranging from 5-50 nM each. Despite their low levels, a test to check whether these compounds could be further reduced was conducted, addressing the possibility that the compositions in terms of concentrations could be optimized.

In order to test whether the dilution of any ingredient in either N-E-O-A or N-E-A-F combination might cause impairment of anti-EV71 potency.

When the combination of only one compound was reduced, none of these new regimens caused significant change of their anti-EV71 efficacy (FIGS. 6 to 9). These results indicate that these regiments can be further optimized by reduction of ingredient concentration. For example, in N-E-O-A regimen, ouabain could be reduced to as low as 0.6 nM and overall inhibitory effects did not have any change (FIG. 7). Likewise, the use of fluoxetine of as low as 6 nM did not change anti-EV71 potency of the original N-E-A-F regiment (FIG. 9). It was also tested to know whether all of the components could be decreased simultaneously without decrease of anti-EV71 effects while one of the ingredients can be further reduced at one time for two quaternary combinations. It was found that simultaneous reduction of all components severely lessened their anti-EV71 efficacy (FIG. 10); when 1:4 diluted regiments were used, no inhibitory effects could be seen. Thus, these data suggest that optimization through reduction of ingredient concentrations is likely a highly complicated process, probably due to the intricate interactions between these components.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any appropriate suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

What is claimed is:

1. A combination for treating an EV71 infection, which comprises two or more compounds at each's non-effective level against EV71 replication, wherein the compounds are selected from the group consisting of auranofin, ouabain, emetine, niclosamide, and S-(+)-fluoxetine;
   wherein the non-effective level of niclosamide is below 2 mg per day for a human subject, the non-effective level of ouabain is below 0.3 mg per day for a human subject, the non-effective level of auranofin is below 6 mg per day for a human subject, the non-effective level of emetine is below 60 mg per day for a human subject, and the non-effective level of S-(+)-fluoxetine is below 20 mg per day for a human subject.

2. The combination of claim 1, which comprises (i) niclosamide, and (ii) emetine, auranofin, ouabain or S-(+)-fluoxetine.

3. The combination of claim 1, which comprises (i) emetine, (ii) and ouabain, auranofin or S-(+)-fluoxetine.

4. The combination of claim 1, which comprises (i) ouabain, and (ii) auranofin or S-(+)-fluoxetine.

5. The combination of claim 1, which comprises auranofin and S-(+)-fluoxetine.

6. A pharmaceutical composition for treating an EV71 infection, comprising the combination of claim 1.

7. A pharmaceutical composition for treating hand, foot and mouth disease (HFMD), comprising the combination of claim 1.

8. The combination of claim 1, which comprises three or more compounds selected from the group consisting of auranofin, ouabain, emetine, niclosamide, and S-(+)-fluoxetine.

9. The combination of claim 1, which comprises four or more compounds selected from the group consisting of auranofin, ouabain, emetine, niclosamide, and S-(+)-fluoxetine.

10. The combination of claim 1, which comprises auranofin, ouabain, emetine, niclosamide, and S-(+)-fluoxetine.

* * * * *